United States Patent
Inoue et al.

(10) Patent No.: US 9,194,781 B2
(45) Date of Patent: Nov. 24, 2015

(54) VISCOELASTICITY MEASURING APPARATUS

(71) Applicants: Tanita Corporation, Itabashi-ku, Tokyo (JP); Tokyo University of Agriculture and Technology, Fuchu-shi, Tokyo (JP)

(72) Inventors: Kazuma Inoue, Tokyo (JP); Atsushi Sakuma, Tokyo (JP)

(73) Assignees: TANITA CORPORATION, Itabashi-Ku, Tokyo (JP); TOKYO UNIVERSITY OF AGRICULTURE AND TECHNOLOGY, Fuchu-Shi, Tokyo (JP)

(*) Notice: Subject to any disclaimer, the term of this patent is extended or adjusted under 35 U.S.C. 154(b) by 36 days.

(21) Appl. No.: 13/828,039

(22) Filed: Mar. 14, 2013

(65) Prior Publication Data

US 2014/0020476 A1 Jan. 23, 2014

(30) Foreign Application Priority Data

Jul. 20, 2012 (JP) ................. 2012-161478

(51) Int. Cl.
| | |
|---|---|
| *G01N 3/00* | (2006.01) |
| *G01N 3/08* | (2006.01) |
| *A61B 9/00* | (2006.01) |
| *G01N 3/42* | (2006.01) |
| *A61B 5/00* | (2006.01) |

(52) U.S. Cl.
CPC ............... *G01N 3/08* (2013.01); *A61B 5/0053* (2013.01); *A61B 5/442* (2013.01); *A61B 9/00* (2013.01); *G01N 3/42* (2013.01); *G01N 2203/0089* (2013.01); *G01N 2203/0094* (2013.01)

(58) Field of Classification Search
CPC ....................................... G01N 3/08
See application file for complete search history.

(56) References Cited

FOREIGN PATENT DOCUMENTS

| | | |
|---|---|---|
| JP | 2000-316818 A | 11/2000 |
| JP | 2009-240374 A | 10/2009 |
| JP | 2011-137667 A | 7/2011 |
| WO | 2005/002428 A1 | 1/2005 |
| WO | 2010/082356 A1 | 7/2010 |

OTHER PUBLICATIONS

Extended European Search Report dated Sep. 24, 2013, issued by the European Patent Office in corresponding European Patent Application No. 13003670.0-1657. (6 pages).

*Primary Examiner* — Lisa Caputo
*Assistant Examiner* — Brandi N Hopkins
(74) *Attorney, Agent, or Firm* — Buchanan Ingersoll & Rooney

(57) ABSTRACT

A viscoelasticity measuring apparatus that measures viscoelasticity of a measurement target with high precision is provided. The measuring apparatus includes: a casing; a surface contact part provided in the casing and brought into surface contact with skin; a ball indenter that moves toward the skin more than the surface contact part and is pushed into the skin; a driving unit that supports the ball indenter and moves the ball indenter toward the skin; a load cell whose right end side is fixed to the casing and left end side supports the driving unit, the load cell detecting a pushing load that pushes the ball indenter into the skin; and a control unit that obtains displacement of the ball indenter.

10 Claims, 11 Drawing Sheets

VISCOELASTICITY MEASURING APPARATUS

This application is based on and claims the benefit of priority from Japanese Patent Application No. 2012-161478, filed on 20 Jul. 2012, the content of which is incorporated herein by reference.

BACKGROUND OF THE INVENTION

1. Field of the Invention

The present invention relates to a viscoelasticity measuring apparatus that measures viscoelasticity of a measurement target.

2. Related Art

A measuring apparatus for measuring viscoelasticity of a measurement target such as human skin has been known heretofore (for example, Japanese Unexamined Patent Application Publication No. 2000-316818, hereinafter referred to as Patent Document 1). In the invention of Patent Document 1, a pressure sensor unit provided with a probe measures a pressure applied to the measurement target by driving a driving unit.

However, in the invention of Patent Document 1, since the driving unit drives the probe and the pressure sensor unit integrally, the driving unit structure is large and its weight is heavy. As a result, the influence of shaking of a measurer's hand holding the measuring apparatus on measuring precision of the pressure sensor becomes greater. In addition, the driving force of an actuator must be greater for the increased weight.

Furthermore, in the invention of Patent Document 1, the distance between the actuator and the probe is large due to the pressure sensor interposed therebetween. This increases axial runout of the actuator and the influence on measuring precision. Additional components such as bearing and coupling for controlling the shaking are thus required, leading to increased cost. The bearing generates slide friction and has an influence on measuring precision especially when handling low pressure.

Moreover, in the invention of Patent Document 1, a spring presses the pressure sensor to prevent shaking and the apparatus is fixed to a ball screw device, so that the sensor fixing state is unstable due to backlash and the like. In order to perform sensing of higher precision, the fixing state of the pressure sensor must be more stable.

For those reasons, the invention of Patent Document 1 is not suitable for high precision measurement that handles minute pressure.

SUMMARY OF THE INVENTION

A problem to be solved by the present invention is to provide a viscoelasticity measuring apparatus that measures viscoelasticity of a measurement target with high precision.

The present invention solves the problem by the following means.

According to a first aspect of the present invention, there is provided a viscoelasticity measuring apparatus comprising a casing; a surface contact part provided in the casing and brought into surface contact with a measurement target; an indenter that moves toward the measurement target over the surface contact part and is pushed into the measurement target; a driving unit that supports the indenter and moves the indenter toward the measurement target; a load detecting unit of which a fixed part side is fixed to the casing and a movable part side supports the driving unit, wherein the load detecting unit detects a pushing load that pushes the indenter into the measurement target; and a displacement obtaining unit that obtains displacement of the indenter.

The above described viscoelasticity measuring apparatus may comprise a control unit, wherein the control unit performs: an indenter pushing process in which the control unit controls the driving unit to position the indenter at a pushing position; and a viscoelasticity calculating process in which the control unit calculate viscoelasticity of the measurement target at the pushing position of the indenter pushing process, based on output from the load detecting unit and the displacement of the indenter obtained by the displacement obtaining unit.

In the above described viscoelasticity measuring apparatus, the driving unit may include a pulse motor; and the control unit may control the pulse motor by outputting a driving pulse, obtains displacement of the indenter based on the driving pulse, and functions as the displacement obtaining unit.

In the above described viscoelasticity measuring apparatus, the control unit may perform the viscoelasticity calculating process by adding displacement of the load detecting unit as displacement of the indenter.

The above described viscoelasticity measuring apparatus may further comprise a contact angle correcting unit that corrects a contact angle of the indenter with respect to a surface of the measurement target to be orthogonal to the surface of the measurement target.

The above described viscoelasticity measuring apparatus may further comprise a contact pressure correcting unit that corrects appropriately pressure of contact between the surface contact part and the measurement target.

In the above described viscoelasticity measuring apparatus, the viscoelasticity measuring apparatus may be used in such a way that a measurer holds the casing and brings the surface contact part into contact with the measurement target, and may further comprise a vibration reducing unit that reduces vibration between the surface contact part and the measurement target.

According to the present invention, a viscoelasticity measuring apparatus that measures viscoelasticity of a measurement target with high precision can be provided.

DETAILED DESCRIPTION OF THE INVENTION

First Embodiment

A first embodiment of the present invention is described hereinafter with reference to the drawings.

Figure 1A:
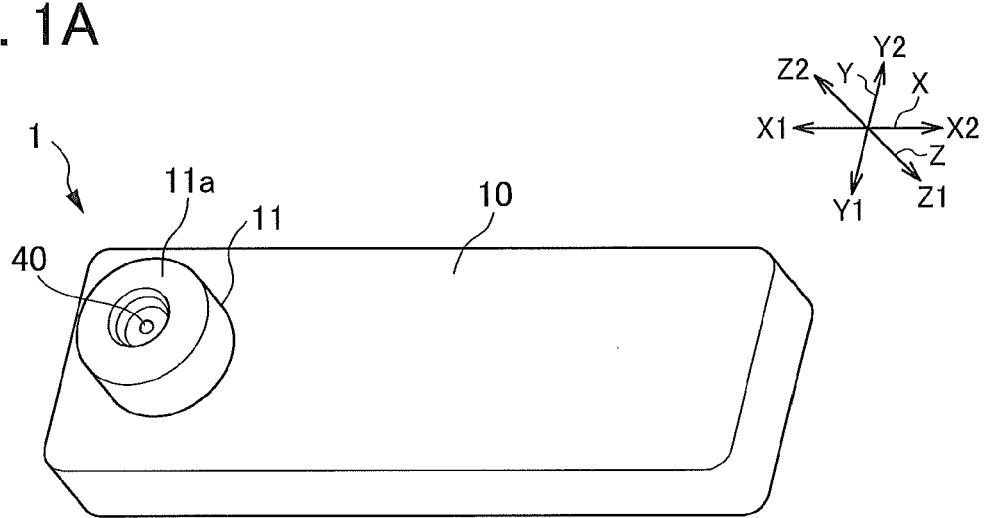
FIG. 1A is a perspective view of a measuring apparatus of a first embodiment.

FIG. 1A is a perspective view of the measuring apparatus 1.

Figure 1B:
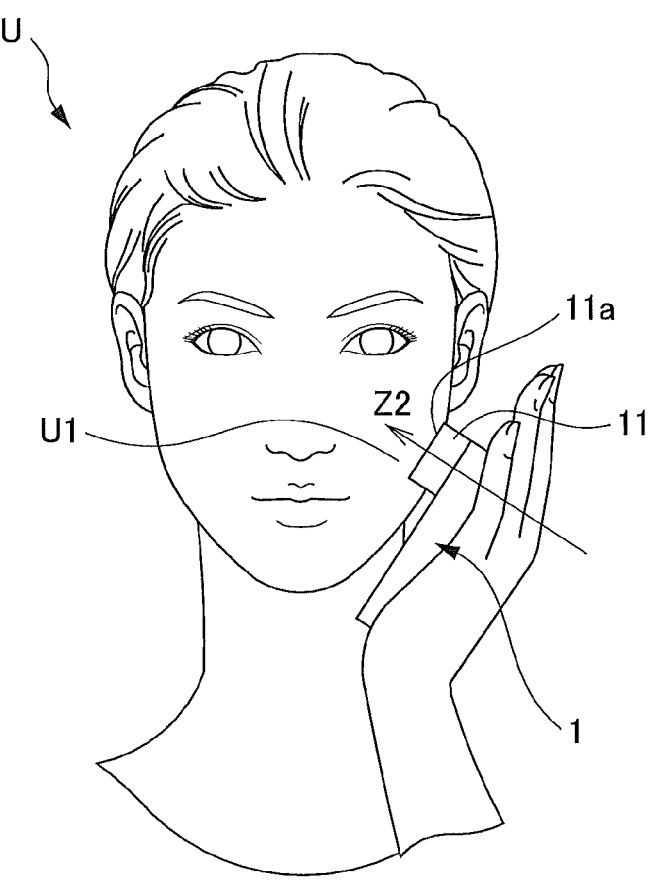
FIG. 1B is a figure illustrating a usage situation of the measuring apparatus of the first embodiment.

FIG. 1B is a figure illustrating a usage situation of the measuring apparatus 1.

In descriptions of the embodiment and drawings, right and left direction, up and down direction, and thickness direction in FIG. 1A are referred to as directions X, Y, and Z.

The measuring apparatus 1 is a cuboid that is elongated in the right and left direction X. The measuring apparatus 1 is sized to fit in the palm of one's hand. The measuring apparatus 1 is a viscoelasticity measuring apparatus that pushes a ball indenter 40 onto the skin U1 and measures viscoelasticity of the skin U1.

A measurer U, who is a user, places the measuring apparatus 1 in his/her palm and puts an annular part 11 against the skin U1 (measurement target) such as the cheek. The measurer U can also grasp the measuring apparatus 1.

By reducing the size of the measuring apparatus 1, the measurer can perform the measurement by putting the measuring apparatus against the cheek while putting a part of his/her palm not used for holding the measuring apparatus 1, against a face. As a result, the influence of shaking of hand can thus be reduced.

Figure 2A:
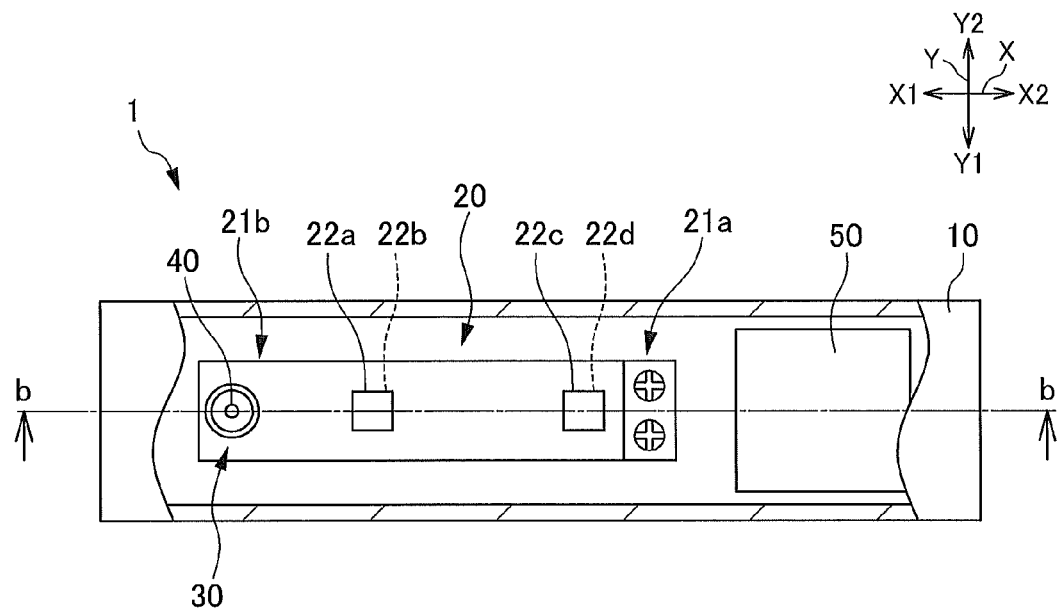
FIG. 2A is a top view of the measuring apparatus of the first embodiment.

FIG. 2A is a top view illustrating an internal configuration of the measuring apparatus 1.

Figure 2B:
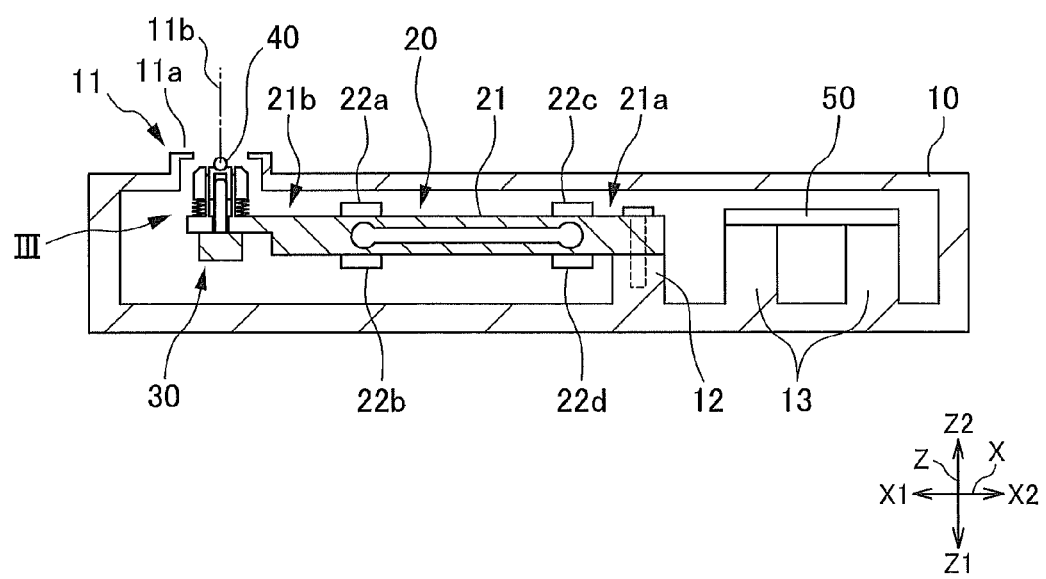
FIG. 2B is a cross-sectional view of the measuring apparatus of the first embodiment.

FIG. 2B is a cross-sectional view taken along the line b-b of FIG. 2A.

Figure 3A:
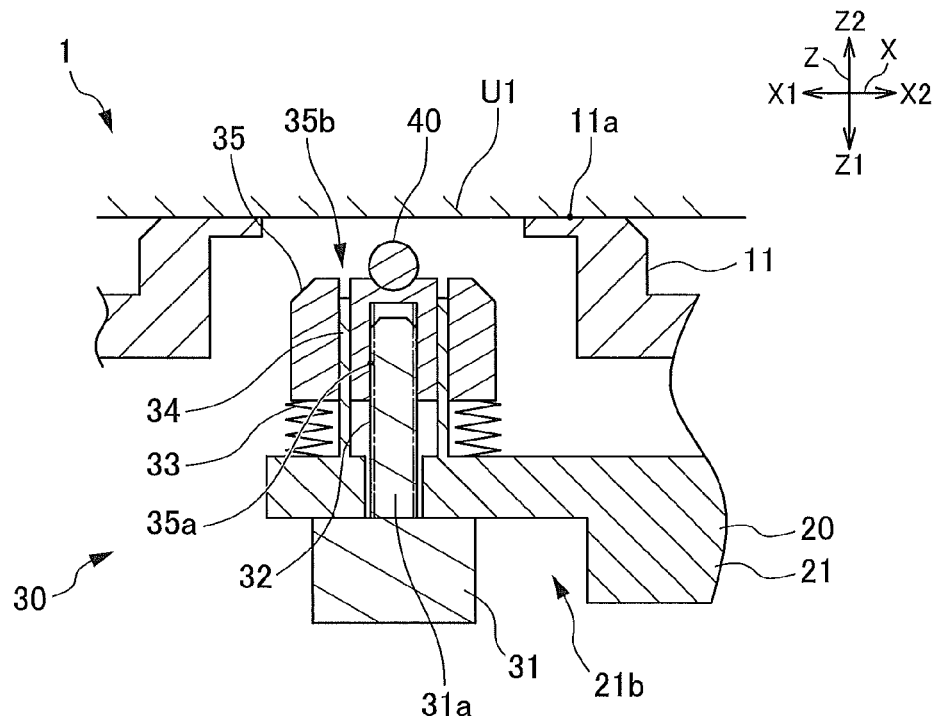
FIG. 3A is an enlarged cross-sectional view of illustrating a vicinity of a driving unit (a part indicated by an arrow III in FIG. 2B) in the first embodiment, in a state in which a ball indenter is positioned at an evacuated position.
Figure 3B:
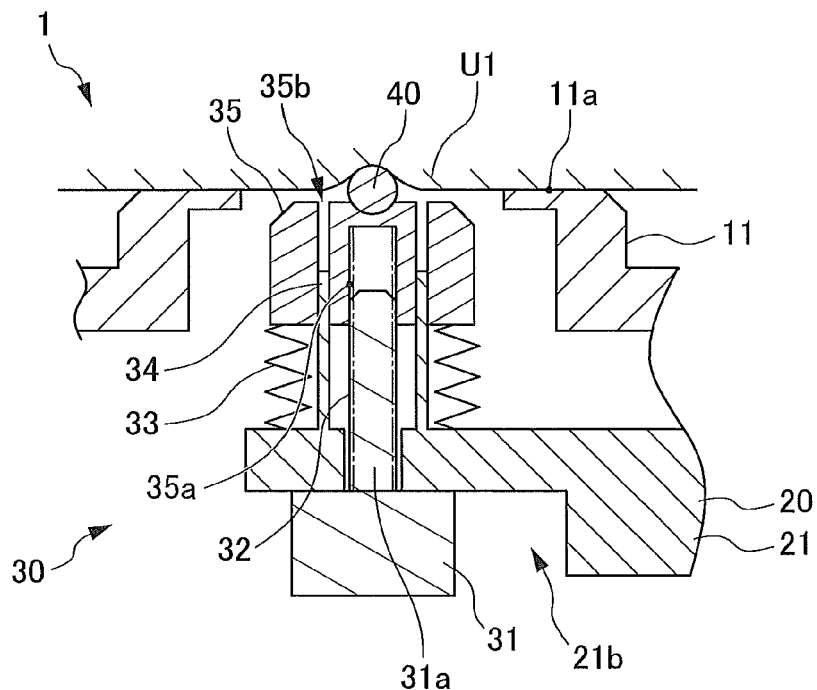
FIG. 3B is an enlarged cross-sectional view illustrating a vicinity of a driving unit (part indicated by an arrow III in FIG. 2B) in the first embodiment, in a state in which the ball indenter is projected.

FIGS. 3A and 3B are enlarged cross-sectional views illustrating a vicinity of a driving unit 30 (a part indicated by the arrow III in FIG. 2B) in the first embodiment.

FIG. 3A illustrates a state in which the ball indenter 40 is positioned at an evacuated position.

FIG. 3B illustrates a state in which the ball indenter 40 is projected.

As shown in FIG. 2, the measuring apparatus 1 includes: a casing 10; the annular part 11; a load cell 20 (load detecting unit); the driving unit 30; the ball indenter 40 (indenter); and a substrate 50.

The casing 10 is a housing of the measuring apparatus 1. The casing 10 is a cuboid that is elongated in the right and left direction X.

The annular part 11 is an annular cylindrical body fixed on a top face of the casing 10. The surface of the annular part 11 is a surface contact part 11a that is brought into surface contact with the user's skin U1. A central shaft 11b of the annular part 11 is parallel to the thickness direction Z.

The load cell 20 detects a load (pressure) applied to the skin U1.

The load cell 20 is configured such that four strain gauges 22a to 22d are attached to an flexure body 21 of a parallel beam shape.

The flexure body 21 is arranged such that a longitudinal direction thereof corresponds to the right and left direction X. A right end side 21a (fixed part side) of the flexure body 21 is fixed by a screw to an attachment boss 12 of the casing 10. A left end side 21b (movable part side) of the flexure body 21 is a free end and supports the driving unit 30.

By the above-described configuration, the load cell 20 measures the load applied to the skin U1 by measuring a load applied in the thickness direction Z to the left end side 21b of the flexure body 21 via the driving unit 30.

The driving unit 30 is designed to support the ball indenter 40 and move the ball indenter 40 in a pushing direction Z2 (toward the measurement target). In the thickness direction Z, a direction toward the annular part 11 of the casing 10 is the pushing direction Z2 and a direction opposite thereto is a retraction direction Z1.

As shown in FIG. 3, the driving unit 30 includes: a pulse motor 31; a feed screw 32; a spring 33; a guide 34; and a moving body 35.

A main body of the pulse motor 31 is fixed to the left end side 21b of the flexure body 21. The axial direction of a rotational shaft 31a of the pulse motor 31 is the thickness direction Z.

The feed screw 32 is a male thread provided on a circumference of the rotational shaft 31a of the pulse motor 31. The feed screw 32 engages with a female screw 35a of the moving body 35. As the feed screw 32 is rotationally driven, the feed screw 32 moves the moving body 35 in the thickness direction Z.

The spring 33 is a helical extension spring that prevents instability caused by clearance gap (e.g. backlash) of the feed screw 32. A lower end of the spring 33 is fixed to the flexure body 21 and an upper end of the spring 33 is fixed to the moving body 35. As a result, the spring 33 pulls the moving body 35 in the retraction direction Z1 (toward the flexure body 21). By providing two springs 33, the moving body 35 can be pulled in an equilibrated manner.

The guide 34 is a shaft body that guides the moving body 35 in a direction parallel to the thickness direction Z. The axial direction of a shaft of the guide 34 is the thickness direction Z. A lower end of the guide 34 is fixed to the left end side 21b of the flexure body 21. The guide 34 is inserted into the guide hole 35b of the moving body 35. Two guides 34 guide the moving body 35 in an equilibrated manner while preventing rotation of the moving body 35 in an X-Y plane.

The moving body 35 is a driven part that is moved by the driving unit 30 in the thickness direction Z, in the above-described configuration. The moving body 35 is formed of resin or the like, and is light-weight.

The ball indenter 40 is a spherical body that is projected from the surface contact part 11a in the pushing direction Z2 and pushed into the skin U1. The ball indenter 40 is fixed to a top face of the moving body 35 and moves in the thickness direction Z along the central shaft 11b of the annular part 11, integrally with the moving body 35.

The ball indenter 40 is bring up from the evacuated position (position shown in FIG. 3A), at which the ball indenter 40 is most retracted with respect to the surface contact part 11a, in the pushing direction Z2, to a position projected from the surface contact part 11a (position shown in FIG. 3B). A movement stroke of the ball indenter 40 is several millimeters.

Here, upon contact of the surface contact part 11a with the skin U1, the skin U1 in a central portion of the surface contact part 11a rises in the Z1 direction, due to a pressure applied to the skin U1. The amount the skin rises depends on the softness of the skin U1 and the force of the measurer holding the measuring apparatus when pushing the measuring apparatus 1 against the skin. This causes variation in contact area between the ball indenter 40 and the skin U1 in relation to the stroke of movement of the ball indenter 40, possibly influencing measurement. For example, in a case in which the amount the skin rises is large, the ball indenter 40 (at the evacuated position shown in FIG. 3A) may already be in contact with the skin U1 when the measurement is begun. On the other hand, in a case in which the amount the skin rises is small, the contact area sufficient for measurement may not be secured.

Given this, a mechanism that moves the annular part 11 in the Z direction can be provided. As a result, the contact area between the ball indenter 40 and the skin U1 can thus be adjusted. Furthermore, for measurement with higher precision, it is preferable to provide a mechanism that can fix the position of the annular part 11 at an adjustment position.

Alternatively, a pressure adjustment unit may be provided, such as a mechanism that maintains pressure applied to the skin U1 within a predetermined range and a mechanism that measures pressure fluctuation. For example, by providing a spring at a position where pressure can be absorbed, and monitoring degree of compression of the spring, the appropriateness of the pressure can be determined; timing for starting the measurement can be realized; and an error massage can be generated in a case in which a large fluctuation is observed during measurement.

With the above-described configuration, the driving unit 30 is only required to drive the ball indenter 40, which is light in weight, in the thickness direction Z without driving the load cell 20, which is heavy in weight. This allows reduction in size and weight of the driving unit 30. The influence of shaking of the hand of the measurer U holding the measuring apparatus 1 during measurement can thus be reduced. In addition, since the driving unit 30 can function with a reduced driving force, driving electricity and power consumption can be reduced.

Furthermore, in the measuring apparatus 1, distance between the driving unit 30 and the skin U1, which is a measurement target, can be reduced. Since this can suppress enhancement of axial runout of the driving unit 30 due to shaking of the hand and the like, the need for components such as a bearing and coupling for controlling the axial runout can be eliminated, and cost reduction can be realized. Moreover, there is no influence of slide friction generated by the bearing and the like, and measuring precision can be improved.

The measuring apparatus 1 is configured such that the load cell 20 is firmly fixed to the attachment boss 12 of the casing 10 by a screw (fixing unit), and the driving unit 30 is provided on the load cell. In the invention of the present application, such a configuration can alleviate a problem being specific to a configuration in which a load sensor is provided on the driving unit as in Patent Document 1. The problems are, that is to say fluctuation of initial load and reduction in repetitive precision that is caused by unstable fixing of a sensor due to backlash and the like.

The fixing means for the fixing unit is not limited to a screw, and an adhesive and the like can also be used.

As shown in FIGS. 2A and 2B, the substrate 50 is a printed-wiring assembly in which a CPU (central processing unit), a semiconductor storage device, or the like, are embedded. The substrate 50 is fixed to the attachment boss 13 of the casing 10. The substrate 50 is electrically connected to electric components of the measuring apparatus 1 via an electric cable and the like (not illustrated). The substrate 50 is also connected to a battery (not illustrated) and supplies power to the electric components.

Figure 4:
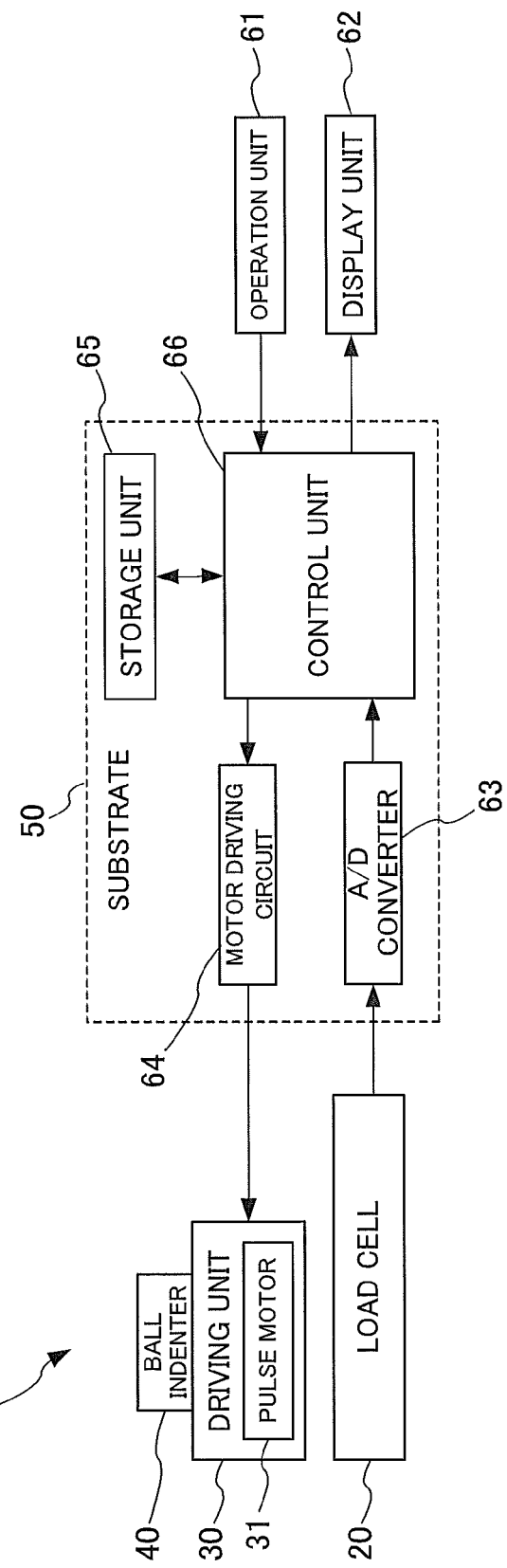
FIG. 4 is a block diagram of the measuring apparatus of the first embodiment.

FIG. 4 is a block diagram of the measuring apparatus 1 of the first embodiment.

The measuring apparatus 1 includes: an operation unit 61; a display unit 62; an A/D converter 63; a motor driving circuit 64; a storage unit 65; and the control unit 66.

The operation unit 61 is provided to allow the measurer U to operate the measuring apparatus 1. The measuring apparatus 1 is provided with an operation button and the like (not illustrated in FIGS. 1 and 2) on the casing 10. The operation unit 61 outputs operation information to the control unit 66.

The display unit 62 is a display device that displays a measurement result. The display unit 62 is provided on the casing 10 (not illustrated in FIGS. 1 and 2).

The A/D converter 63 is an electric circuit that converts an analog signal from the load cell 20 into a digital signal and outputs to the control unit 66. The A/D converter 63 is embedded in the substrate 50.

The motor driving circuit 64 is a driving circuit of the pulse motor 31. The motor driving circuit 64 outputs voltage and the like suitable for driving of the pulse motor 31 based on a driving pulse output by the control unit 66. The motor driving circuit 64 is embedded in the substrate 50.

The storage unit 65 is a storage device for storing a program, information, and the like required for operation of the measuring apparatus 1. The storage unit 65 is composed of a storage device and the like installed on the substrate 50.

The control unit 66 is a control device that controls the measuring apparatus 1 in an overall manner. The control unit 66 is composed of a CPU and the like installed on the substrate 50.

The control unit 66 computes load of the load cell 20 based on an output from the A/D converter 63. The control unit 66 outputs a driving pulse to control the pulse motor 31 and counts the number of pulses of the driving pulse to obtain the displacement of the ball indenter 40. In other words, the control unit 66 also functions as the displacement obtaining unit that obtains displacement of the ball indenter 40.

Figure 5:
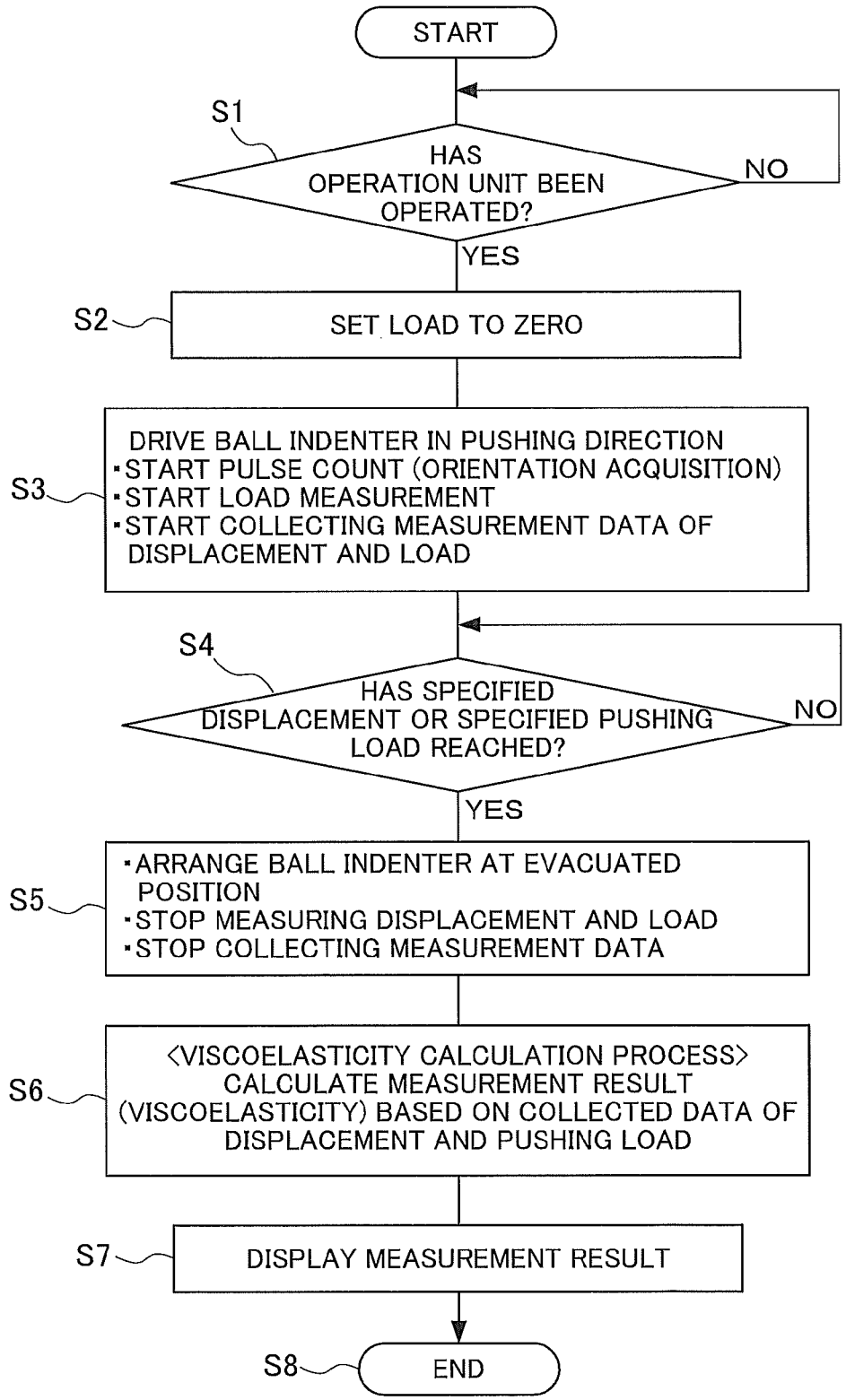
FIG. 5 is a flow chart of processing of the measuring apparatus of the first embodiment.

FIG. 5 is a flow chart of processing of the measuring apparatus 1 of the first embodiment.

Upon beginning measurement, the measurer U brings the surface contact part 11a in the annular part 11 of the measuring apparatus 1 into light contact with the skin U1. This state is shown in FIG. 3A. The measurer U operates the operation unit 61 in this state.

In step (hereinafter simply referred to as S) S1, the control unit 66 determines whether to start measurement or not, based on an output from the operation unit 61. In a case in which the control unit 66 determines to start measurement (S1: YES), the processing advances to S2. On the other hand, in a case in which the control unit 66 determines not to start measurement (S1: NO), the processing of S1 is repeated.

In S2, after the operation, the control unit 66 initializes (setting to zero) the load applied to the load cell 20 when the surface contact part 11a is put against the skin U1, which is the measuring target.

In S3, the control unit 66 outputs the driving pulse to drive the pulse motor 31. Upon starting driving of the pulse motor 31, the control unit 66 starts counting the driving pulses and obtains the displacement of the ball indenter 40 based on the number thus counted, and starts measuring the load by the load cell 20.

As shown in FIG. 3, the ball indenter 40 thus moves in the pushing direction Z2 and makes contact with the skin U1.

The control unit 66 continues to measure the displacement and pushing load at predetermined sampling intervals until reaching specified displacement or specified pushing load, and accumulates data.

In S4, the control unit 66 determines whether the pushing load has reached the specified pushing load or not, or whether the displacement of the ball indenter 40 has reached the specified displacement or not. In a case in which the control unit 66 determines that any of these conditions has been satisfied (S4: YES), the processing advances to S5. On the other hand, in a case in which the control unit 66 determines that none of these conditions has been satisfied (S4: NO), the processing of S4 is repeated. The processing of S4 is repeated until the pushing load reaches the specified pushing load or the displacement of the ball indenter 40 reaches the specified displacement (S4: YES).

In S5, the control unit 66 drives the ball indenter 40 in the retraction direction Z1 and positions at the evacuated position (see FIG. 3A). Meanwhile, the control unit 66 stops measurement of displacement and load, and terminates accumulation of data.

In S6, the control unit 66 performs a viscoelasticity calculating process. In this process, the control unit 66 calculates viscoelasticity of the skin U1 based on the accumulated data relating to displacement and load. A method for this calculation can be selected from among various calculation methods. For example, using Equations 28, 26 and 31 in Japanese Unexamined Patent Application Publication No. 2011-137667, non-linear physical properties of a three element solid model can be obtained: a Young's modulus of an elastic portion; viscosity compliance of a viscoelastic portion; and Young's modulus of an elastic portion in the viscoelastic portion. The equations corresponding to the above-cited equations 28, 26 and 31 respectively are as follows.

[Equation 1]

$$E^e(\varepsilon_k^e) := \frac{\dot{\sigma}_{\alpha k}}{\dot{\varepsilon}_\alpha - C(\varepsilon_k^v) \cdot (\overline{\sigma}_{k+1} - \sigma_{\alpha k}^{ve})} \quad \text{Equation 28}$$

$$C(\varepsilon_k^v) := \frac{\dot{\sigma}_{\beta k}\dot{\varepsilon}_\alpha - \dot{\sigma}_{\alpha k}\dot{\varepsilon}_\beta + (1-R_k)\dot{\sigma}_{\alpha k}(\overline{\sigma}_{k+1} - \sigma_{\beta k}^{ve})C(\varepsilon_{k-1}^v)}{\dot{\sigma}_{\beta k}(\overline{\sigma}_{k+1} - \sigma_{\alpha k}^{ve}) - R_k\dot{\sigma}_{\alpha k}(\overline{\sigma}_{k+1} - \sigma_{\beta k}^{ve})} \quad \text{Equation 26}$$

-continued $$E^{ve}(\varepsilon_k^v) := \quad \text{Equation 31}$$

$$E^{ve}(\varepsilon_{k-1}^v) + \frac{\varepsilon_{\alpha k}^v - \varepsilon_{k-1}^v}{\varepsilon_{\gamma k}^v - \varepsilon_{k-1}^v}\left(\frac{E^e(\varepsilon_k^e)E_{\gamma k}}{E^e(\varepsilon_k^e) - E_{\gamma k}} - E^{ve}(\varepsilon_{k-1}^v)\right)$$

here: $R_k = \dfrac{\varepsilon_{\beta k}^v - \varepsilon_{k-1}^v}{\varepsilon_{\alpha k}^v - \varepsilon_{k-1}^v}$ E: Young's modulus
C: viscosity compliance
ε: strain
$\dot{\varepsilon}$: strain rate
τ: stress
$\dot{\tau}$: stress rate The indices e, v, and ve respectively represent the elastic portion, the viscoelastic portion, and the elastic portion in the viscoelastic portion.

$\dot{\varepsilon}_\alpha(\varepsilon_\alpha \text{dot}), \dot{\varepsilon}_\beta(\varepsilon_\beta \text{dot}), \dot{\varepsilon}_\gamma(\varepsilon_\gamma \text{dot})$ The above equation is a strain rate with a relationship of (εα dot)>(εβ dot)>(εγ dot), in which (εα dot) and (εβ dot) represent relatively high strain rates and (εγ dot) represents a strain rate extremely low compared to the (εα dot) and (εβ dot).

In addition, in the embodiments, the measurement target is the skin U1, which is thin. Given this, using Equations 31 and 34 in PCT International Application Publication No WO2010/084840 that are suitable for a thin measurement target, Young's modulus E was obtained as elasticity of the skin U1. The components in the present embodiment corresponding to the above-cited equations 31 and 34, respectively, are as follows.

[Equation 3]

$$\hat{F} = \frac{4}{3}\frac{E}{1-\nu^2}\left(\frac{\phi}{2}\right)^{\frac{1}{2}}\{\delta(1+B\delta)\}^{\frac{3}{2}} \quad \text{Equation 31}$$

$$E = -\frac{6}{\pi^3(1-\nu^2)^2}\left(\frac{2}{\phi}\right)^2\frac{\hat{F}}{\varepsilon_l^3} \quad \text{Equation 34}$$

δ: displacement from the position where the ball indenter 40 contact with the skin U1
$\hat{F}$: pushing load of the specimen having finite thickness
φ: diameter of the ball indenter 40
ν: Poisson ratio of the skin U1
B: factor which indicate influence of load which increase with the pushing
$\bar{\varepsilon}_l$: corresponding pushing strain It should be noted that, in a case in which displacement of a left end side 20b of the load cell 20 due to pressing of the ball indenter 40 cannot be ignored, the control unit 66 can be configured to correct the displacement, which is based on the driving pulse, by adding the displacement of the left end side 20b. In this case, the displacement of the left end side 20b and the output from the load cell 20 may be measured and stored in the storage unit 65 in advance.

The control unit 66 can then read the displacement of the left end side 20b from the storage unit 65 based on the output from the load cell 20.

In S7, the control unit 66 outputs a viscoelasticity measurement result on the display unit 62. Alternatively, in order to allow the measurer U to check the measurement result afterward, the control unit 66 can be configured to store the measurement result in the storage unit 65, so as to be readable according to an operation of the operation unit 61.

In S8, the control unit 66 terminates a set of processes.

All or some functions of: the operation unit 61, the display unit 62, the storage unit 65, and the control unit 66 can be realized by an external device such as a PC (personal computer) connected to the measuring apparatus 1. Alternatively, both the measuring apparatus 1 and the external device can have these functions.

For example, for an operation of starting measurement performed on the operation unit 61, a switch for starting measurement can be provided in the measuring apparatus 1, and a button for submitting a command for starting measurement to communication software or the like can be provided in the external device. This allows the measurer to select the operation of starting measurement based on measurement scenes.

A circuit for communication between the measuring apparatus 1 and the external device is provided on the substrate 50. Connection between the measuring apparatus 1 and the external device can be realized either in a wired manner (RS-232C, USB, and the like) or in a wireless manner (Bluetooth (registered trademark), Wi-Fi (registered trademark), and the like).

As described above, the measuring apparatus 1 according to the present embodiment can improve the measuring precision by arranging the driving unit 30 on the movable end side of the load cell 20. Since the control unit 66 obtains the displacement of the ball indenter 40 based on the driving pulse of the pulse motor 31, a configuration of the measuring apparatus can be simplified.

Second Embodiment

A second embodiment of the present invention is described hereinafter.

In the description and drawings of the following embodiments, components with similar functions to those of the first embodiment are referred to by the same numerals or numerals with the same last two digits, and a detailed description thereof will be omitted accordingly.

Figure 6A:
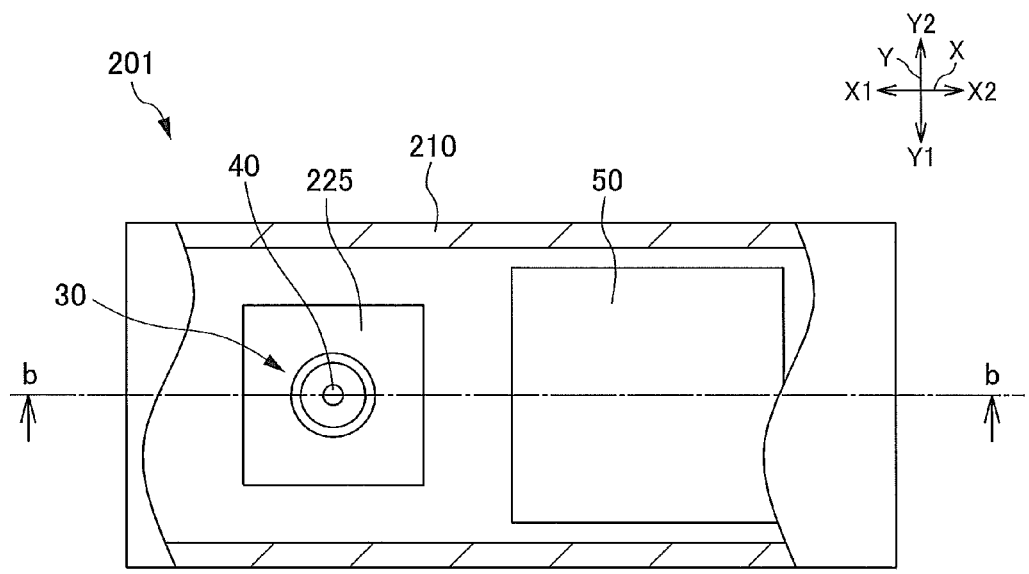
FIG. 6A is a top view of the measuring apparatus of a second embodiment.
Figure 6B:
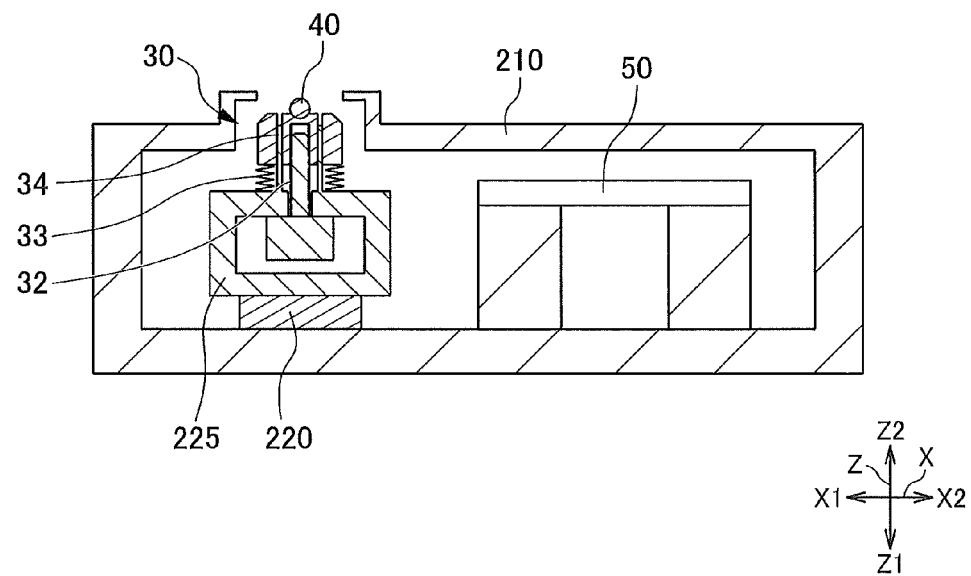
FIG. 6B is a cross-sectional view of the measuring apparatus 201 of the second embodiment (corresponding to FIG. 2)

FIGS. 6A and 6B are a top view and a cross-sectional view of a measuring apparatus 201 of the second embodiment (corresponding to FIGS. 2A and 2B).

The measuring apparatus 201 is provided with a load sensor 220 and a chassis 225.

As the load sensor 220, a small-sized piezoelectric element in a cylindrical shape or the like is used. A lower face (fixed end side) of the load sensor 220 is fixed to a bottom face of a casing 210. To an upper face (movable end side) of the load sensor 220, the chassis 225 is fixed.

The chassis 225 functions as a base for attachment of a driving unit 30.

In the above-described configuration, in the measuring apparatus 201, the load sensor 220 measures the pushing load of the ball indenter 40 via the driving unit 30, as in the first embodiment.

As described above, since the measuring apparatus 201 uses the piezoelectric element as the load sensor 220, the entire apparatus can be reduced in size.

Third Embodiment

A third embodiment of the present invention is described hereinafter.

Figure 7A:
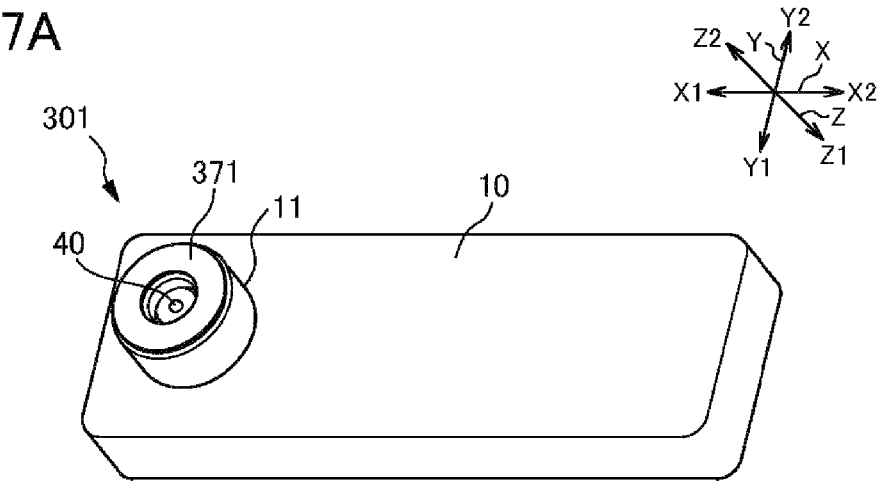
FIG. 7A is a perspective view of a measuring apparatus of a third embodiment.
Figure 7B:
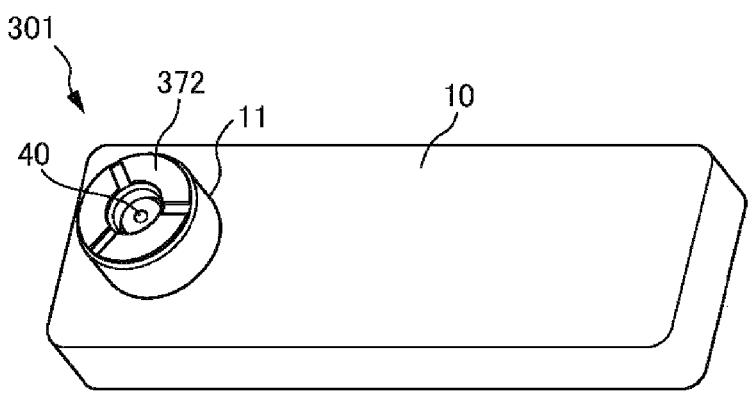
FIG. 7B is a perspective view of the measuring apparatus of the third embodiment.
Figure 7C:
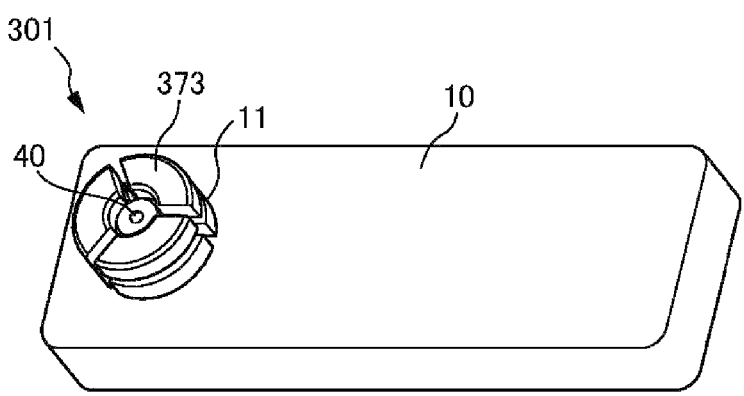
FIG. 7C is a perspective view of the measuring apparatus of the third embodiment.

FIGS. 7A, 7B and 7C are perspective views of measuring apparatus 301 of the third embodiment.

As shown in FIG. 7A, the measuring apparatus 301 is provided with an adhesive sheet 371.

The adhesive sheet 371 is provided at a top end of an annular part 11. The adhesive sheet 371 adheres to the skin during measurement. The measuring apparatus 301 can thus correct a contact angle of a ball indenter 40 with the skin, and can make the top end of the annular part 11 (surface contact part) adhere to the skin surface even when the measurer's hand or body shakes, thereby reducing influence of the shaking on the measurement.

As shown in FIG. 7B, the measuring apparatus 301 is provided with three pressure sensors 372.

The pressure sensors 372 are arranged in the top end of the annular part 11 at predetermined intervals. The pressure sensors 372 output pressure information being detected to a control unit 66 (see FIG. 4). The control unit 66 starts measurement when output differences of the three pressure sensors 372 are within a predetermined range.

As the result, the measuring apparatus 301 can start the measurement only when the contact angle of a ball indenter 40 is corrected to a value within a predetermined range. As the measurement can be performed with appropriate contact pressure between a surface contact part and the skin, measurement error due to hardened skin as a result of excessive contact pressure can be curtailed.

The control unit 66 can also be configured to alert (notify) the measurer of the possibility of an incorrect measurement result with sound or light, in a case in which the output differences of the pressure sensors 372 or the gravity centers of the pressure sensors 372 are not within a predetermined range.

Alternatively, the pressure sensors 372 can be a single annular member, not the three separate members. Also in this case, since the control unit 66 is configured to start the measurement when the sensor output is within an appropriate range, the measuring apparatus 301 can start the measurement only when the contact angle of the ball indenter 40 is corrected to a value within a predetermined range. As the measurement can be performed with appropriate contact pressure between the surface contact part and the skin, measurement error due to hardened skin as a result of excessive contact pressure can be curtailed. Furthermore, this configuration allows reduction in the number of components.

As shown in FIG. 7C, the measuring apparatus 301 is provided with three switches 373.

The switches 373 are arranged in the top end of the annular part 11 at predetermined intervals. The switches 373 are arranged to activate an electrical contact thereinside upon depression by a predetermined amount to the retraction direction Z1, and to output a signal to the control unit 66 (see FIG. 4). The control unit 66 starts the measurement only when the signal is output from the three switches 373.

As the result, the measuring apparatus 301 can start the measurement only when the contact angle of the ball indenter 40 is corrected to a value within a predetermined range.

FIGS. 8A-8D are perspective views and cross-sectional views of the measuring apparatus 301 of the third embodiment.

Figure 8A:
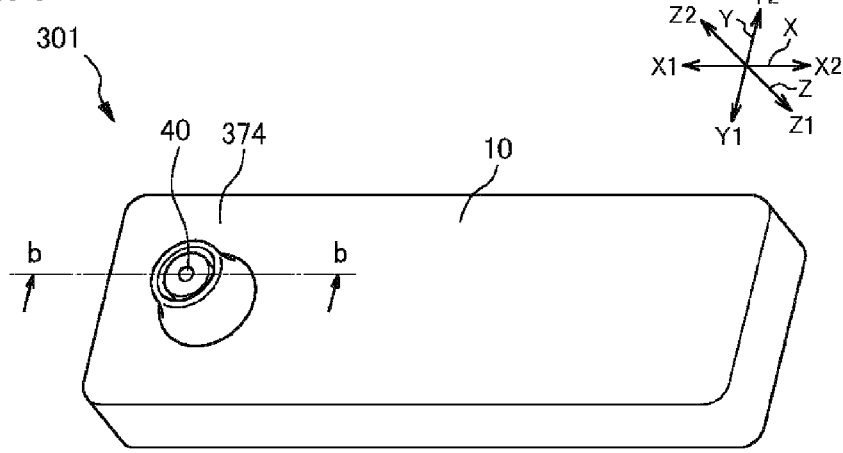
FIG. 8A is a perspective view of a measuring apparatus of the third embodiment.

FIG. 8A is a perspective view of the measuring apparatus 301.

Figure 8B:
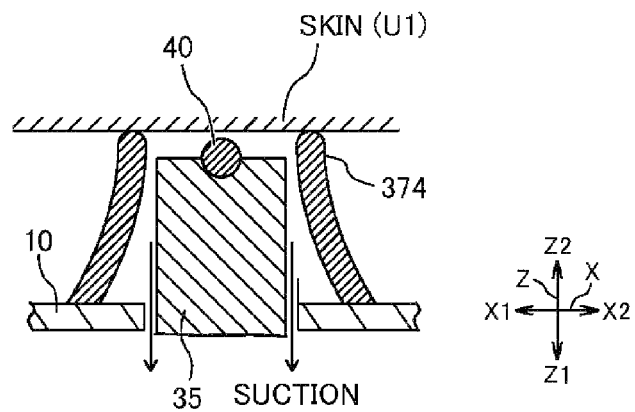
FIG. 8B is a cross-sectional view of the measuring apparatus of the third embodiment.

FIG. 8B is an enlarged cross-sectional view taken along the line b-b of FIG. 8A.

Figure 8C:
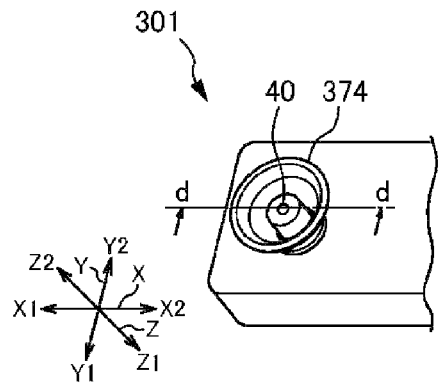
FIG. 8C is another perspective view of the measuring apparatus of the third embodiment.
Figure 8D:
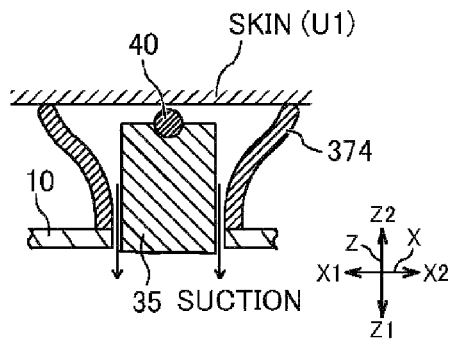
FIG. 8D is another cross-sectional view of the measuring apparatus of the third embodiment.

FIGS. 8C and 8D are a perspective view and a cross-sectional view of other aspects of the measuring apparatus 301 of the third embodiment.

As shown in FIGS. 8A and 8B, the measuring apparatus 301 is provided with a suction nozzle 374 instead of the annular part.

The measuring apparatus 301 activates a suction pump or the like (not illustrated) to suction the air, in a state in which the suction nozzle 374 is in contact with the skin U1, to thereby bring the skin U1 into close contact with an edge of the suction nozzle 374.

Accordingly, the measuring apparatus 301 can correct the contact angle of the ball indenter 40 to the skin U1.

The measuring apparatus 301 can make the top end of the suction nozzle 374 (surface contact part) adhere to the skin surface even when the measurer's hand or body shakes, thereby reducing influence of the shaking on the measurement.

It should be noted that the suction nozzle 374 can be configured to increase in diameter as it comes closer to the top end thereof, as shown in FIGS. 8C and 8D.

Figure 9A:
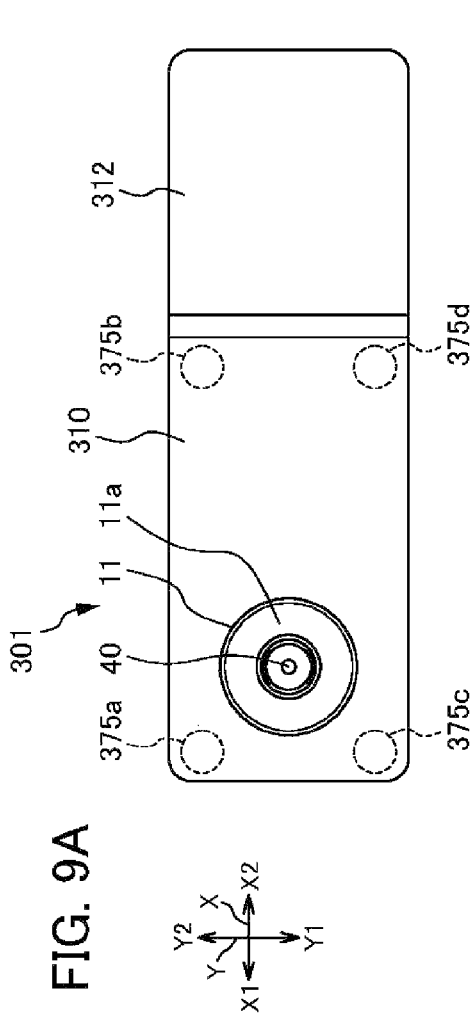
FIG. 9A is one of a three-view drawing of the measuring apparatus of the third embodiment.
Figure 9B:
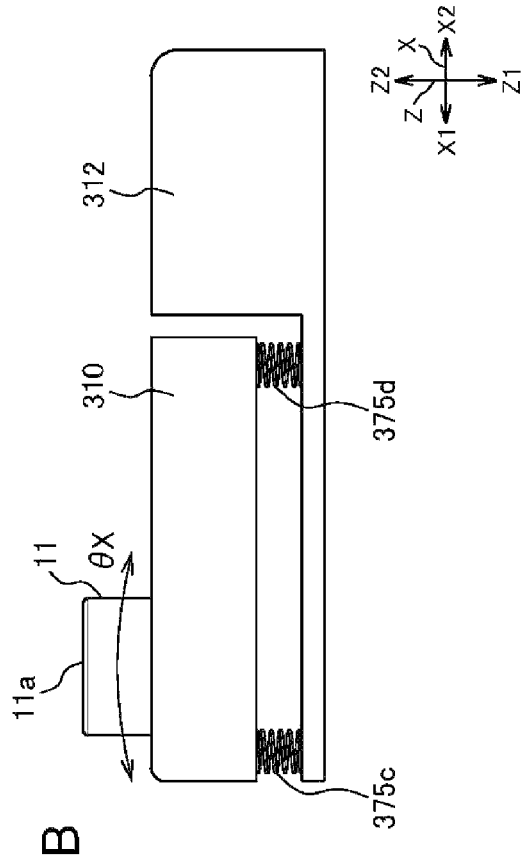
FIG. 9B is one of a three-view drawing of the measuring apparatus of the third embodiment.
Figure 9C:
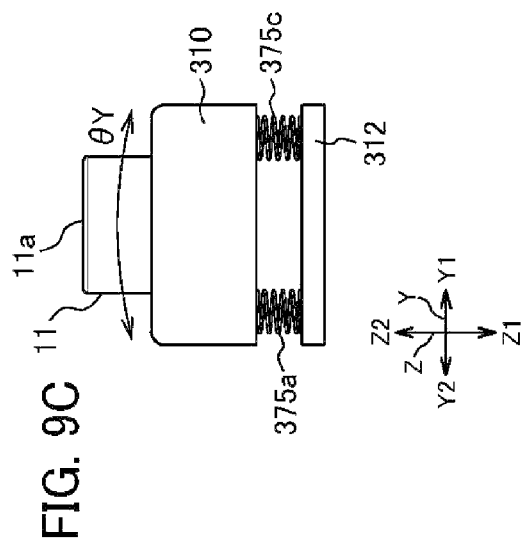
FIG. 9C is one of a three-view drawing of the measuring apparatus of the third embodiment.

FIGS. 9A-9C are three-view drawings of the measuring apparatus 301 of the third embodiment.

The measuring apparatus 301 includes the casing 310, a grip part 312, and four springs 375a to 375d.

The casing 310 is a member similar to the casing 10 of the first embodiment and houses a load cell, a driving unit and the like as in the first embodiment.

The grip part 312 is a housing that supports the casing 310. During measurement, the measurer places the grip part 312 in his/her palm or grasps the grip part 312 to put the surface contact part 11a against the skin.

The springs 375a to 375d are helical springs provided between the casing 310 and the grip part 312. Lower ends of the springs 375a to 375d are fixed to the grip part 312. Upper ends of the springs 375a to 375d are fixed to bottom corner portions of the casing 310.

As the springs 375a to 375d are compressed and extended, the casing 310 is rotatably supported in rotational directions θX and θY with respect to the grip part 312.

As a result, in the measuring apparatus 301, when the surface contact part 11a is in contact with the skin, the casing 310 rotates to correct the contact angle of the ball indenter 40 with respect to the skin surface. In addition, this can absorb the vibration between the surface contact part 11a and the skin due to hand shaking and body movement during measurement, thereby reducing the influence of vibration on the measurement.

Furthermore, the measurer does not hold the casing 310 directly during measurement. As a result, the measuring apparatus 301 can reduce strain of the casing 310 due to holding by the measurer, thereby reducing strain of the load cell caused by the strain of the casing 310. As a result, the measuring apparatus 301 can further improve the measuring precision.

The springs 375a to 375d can be other elastic members. For example, a blade spring and rubber can be used instead of the springs 375a to 375d.

Furthermore, by providing a sensor that detects compression of the springs exceeding a preset amount, the control unit 66 (see FIG. 4) can be configured to not perform measurement in response to output from the sensor, and if an alert (notice) is given to the measurer concerning the possibility of an incorrect measurement result with sound or light, it is possible to curtail measurement error due to hardened skin as a result of excessive contact pressure.

Figure 10A:
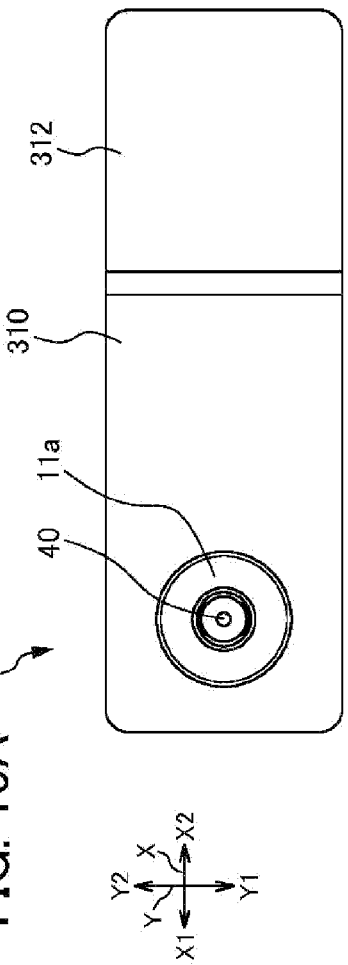
FIG. 10A is one of a three-view drawing of the measuring apparatus of the third embodiment.
Figure 10B:
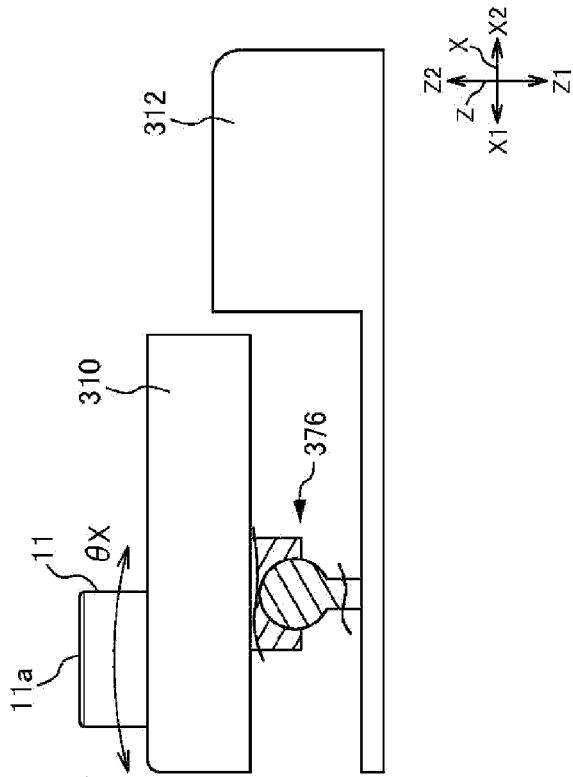
FIG. 10B is one of a three-view drawing of the measuring apparatus of the third embodiment.
Figure 10C:
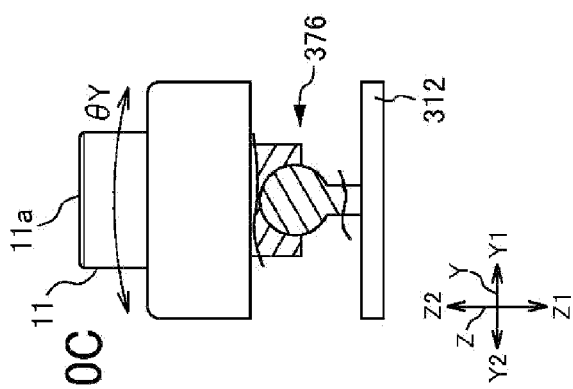
FIG. 10C is one of a three-view drawing of the measuring apparatus of the third embodiment.

FIGS. 10A-10C are three-view drawings of the measuring apparatus 301 of the third embodiment.

The measuring apparatus 301 includes the casing 310, the grip part 312, and a ball joint 376.

While the measuring apparatus 301 is configured such that the springs 375a to 375d connect the casing 310 with the grip part 312, the measuring apparatus 301 is configured such that the connection is realized by the ball joint 376.

As a result, the measuring apparatus 301 can correct the contact angle of the ball indenter 40 with respect to the skin surface, reduce the influence of vibration between the surface contact part 11a and the skin, and reduce strain of the casing thereby improving the measurement precision, by not making the measurer directly hold the casing that houses the load cell.

Figure 11:
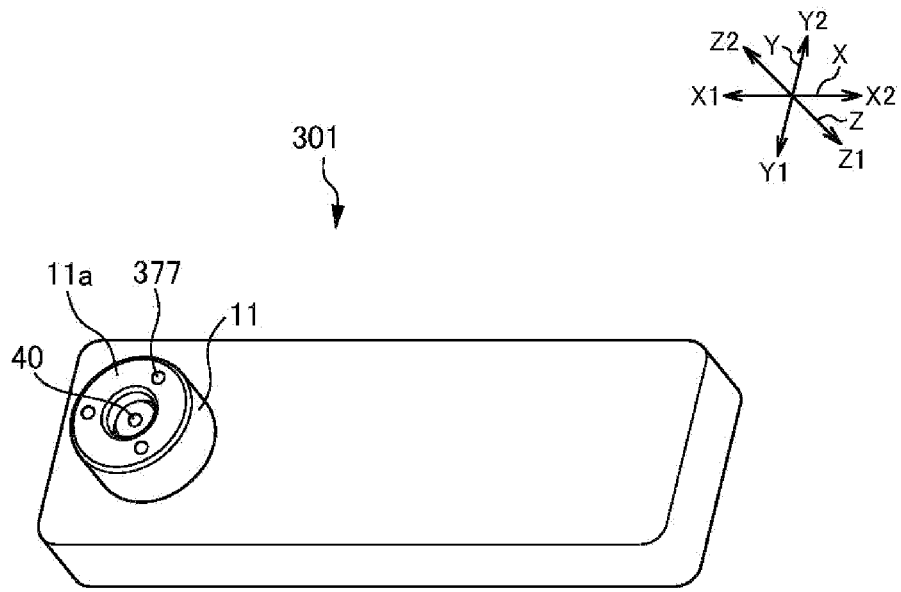
FIG. 11 is a perspective view of the measuring apparatus of the third embodiment.

FIG. 11 is a perspective view of the measuring apparatus 301 of the third embodiment.

The measuring apparatus 301 is provided with three projections 377.

The projections 377 are provided on the surface contact part 11a at a top end of the circular part 11, at equal intervals. The projections 377 project from the surface contact part 11a.

The measurer can thus check a sensation of the projections 377 in contact with the skin to thereby correct the degree of contact with the surface contact part 11a.

As a result, the measuring apparatus 301 can correct the contact angle of the ball indenter with respect to the skin surface.

In addition, by providing an acceleration sensor and a load sensor (load difference detection unit), the influence of load difference due to hand shake and the like can be suppressed, thereby improving measurement precision. The load sensor detects load variation with respect to an initial load at the beginning of measurement. The initial load is defined by an angle of the measuring apparatus (x, y, z directions). Hand shaking changes the angle from the initial position and the initial load, leading to an error in a load value. The acceleration sensor and the load sensor detect and correct such an error.

For example, in a case in which the acceleration sensor is provided, change of the initial load is estimated and corrected based on the initial position and acceleration information relating to hand shaking.

On the other hand, in a case in which the load sensor is provided, in addition to the load sensor for measurement, a load sensor for correction should be provided of which detection direction is the same as that of the load sensor for measurement. The initial load of the load sensor for correction is adjusted by making it the same as that of the load sensor for measurement, or by multiplying the load value by a coefficient. By subtracting an output of the load sensor for correction from an output of the load sensor for measurement, a measurement error caused by angle variation from the initial position due to hand shaking and the like can be cancelled, and only a load applied on the ball indenter 40 can be extracted. According to the above-described embodiments, it is only required to drive the ball indenter 40, which is light in weight, without driving the load detection unit, which is heavy in weight. This allows reduction in size and weight of the driving unit. As a result, the influence of shaking of the hand of the measurer holding the measuring apparatus during measurement can thus be reduced. In addition, since the driving unit can function with a reduced driving force, driving electricity and power consumption can be reduced.

Furthermore, the distance between the driving unit and the measurement target can be reduced. This can suppress axial runout of the driving unit due to shaking of the hand and the like, eliminating the need for components such as a bearing and coupling for controlling the axial runout, and cost reduction can be realized. Moreover, there is no influence of slide friction generated by the bearing and the like, and measuring precision can be improved.

In addition, since the load sensor can be firmly fixed to the housing of the measuring apparatus, the measurement precision of the load sensor can be improved.

According to the above-described embodiments, the control unit can calculate viscoelasticity of the measurement target based on an output from the load detection unit and displacement of the indenter at the pressure position of the indenter.

According to the above-described embodiments, since the control unit obtains the displacement of the indenter based on the driving pulse of the pulse motor, configuration of the measuring apparatus can be simplified.

According to the above-described embodiments, since the displacement of the load detection unit itself is added as the displacement of the indenter, the measurement precision can further be improved.

According to the above-described embodiments, since the contact angle of the indenter is corrected, the measurement precision can further be improved.

According to the above-described embodiments, since the pressure of contact between the surface contact part and the measurement target is appropriately corrected, precision of load detection and displacement obtention can be improved, thereby improving measurement precision.

According to the above-described embodiments, since vibration between the surface contact part and the measurement target, stable load detection and displacement obtention can be realized even with hand shaking and body movement of the measurer, thereby improving measurement precision.

The embodiments of the present invention have been described above; however, the present invention is not limited thereto and various changes can be made such as modifications presented below, and such changes are also within the scope of the present invention. In addition, the effects mentioned in the embodiments are merely examples of most desirable effects provided by the present invention, and the present invention is not limited thereto. It should be noted that the above-described embodiments and the modification can be used in combination accordingly, of which a detailed description is omitted.

Modifications (1) In the embodiments, the control unit is provided in the measuring apparatus main body; however, the present invention is not limited thereto. For example, the measuring apparatus can be connected to a control device such as a personal computer, and a CPU or the like of the control device can be used as the control unit.

(2) In the embodiments, the control unit obtains the displacement of the ball indenter based on the driving pulse of the pulse motor; however, the present invention is not limited thereto. For example, by providing a detection unit such as an optical sensor that detects displacement of the ball indenter, the control unit can be configured to obtain the displacement of the ball indenter based on output from the detection unit.

(3) In the embodiments, the human skin has been exemplified as the measurement target; however, the present invention is not limited thereto. The measuring apparatus according to the embodiments is suitable for soft or thin measurement targets, for example foodstuffs, fibers, rubber, and the like.

(4) In the embodiments, if a noise is generated in output from the load cell (for example, a noise caused by vibration of the load cell accompanying driving of the pulse motor), a filter for cancelling the noise can be provided.

(5) In the embodiments, an example in which the driving unit is disposed directly on the load cell has been presented; however, the present invention is not limited thereto. For example, the present invention can be configured such that a driving unit fixing part is fixed to a left end part (movable part) side of the load cell and the driving unit is fixed to the driving unit fixing part that is positioned more to the left than the left end part of the load cell. This configuration has an advantage of reducing steps for processing the existing load cell.

(6) In the embodiments, an example in which the indenter has a ball shape has been presented; however, the present invention is not limited thereto.

What is claimed is:

1. A viscoelasticity measuring apparatus comprising:
a casing having a longitudinal axis in a first direction;
a surface contact part provided in the casing and brought into surface contact with a measurement target;
an indenter configured to move toward the measurement target over the surface contact part and to be pushed into the measurement target;
a driving unit that supports the indenter and is configured to move the indenter toward the measurement target;
a load detecting unit, including a flexure body and strain gauges attached thereto, configured to detect a pushing load that pushes the indenter into the measurement target in a second direction, the second direction intersecting with the first direction;
a displacement obtaining unit that obtains displacement of the indenter when the indenter is pushed into the measurement target; and
a control unit configured to receive output from the load detecting unit and from the displacement obtaining unit and to calculate the viscoelasticity of the measurement target based on the pushing load detected by the load detecting unit and the displacement obtained by the displacement obtaining unit.

2. The viscoelasticity measuring apparatus according to claim 1, wherein the control unit is configured to:
control the driving unit to position the indenter at a pushing position; and
calculate viscoelasticity of the measurement target at the pushing position, based on output from the load detecting unit and the displacement of the indenter obtained by the displacement obtaining unit.

3. The viscoelasticity measuring apparatus according to claim 2, wherein:
the driving unit includes a pulse motor which is controlled by outputting a driving pulse; and
the displacement obtaining unit is configured to obtain displacement of the indenter based on the driving pulse.

4. The viscoelasticity measuring apparatus according to claim 2, wherein:
the control unit is configured to calculate the viscoelasticity by adding displacement of the load detecting unit as displacement of the indenter.

5. The viscoelasticity measuring apparatus according to claim 1, further comprising:
a contact angle correcting unit configured to correct a contact angle of the indenter with respect to a surface of the measurement target to be orthogonal to the surface of the measurement target.

6. The viscoelasticity measuring apparatus according to claim 1, further comprising:
a contact pressure correcting unit configured to correct appropriately pressure of contact between the surface contact part and the measurement target.

7. The viscoelasticity measuring apparatus according to claim 1, the viscoelasticity measuring apparatus being used in such a way that a measurer holds the casing and brings the surface contact part into contact with the measurement target, and further comprising a vibration reducing configured to reduce vibration between the surface contact part and the measurement target.

8. The viscoelasticity measuring apparatus according to claim 1, wherein the indenter is spherically shaped and the control unit is configured to calculate the viscoelasticity of the measurement target further based on the diameter of the spherically-shaped indenter.

9. The viscoelasticity measuring apparatus according to claim 1, wherein the casing has substantially cuboid shape with three pairs of aspects, each of the three pairs having an area of different magnitude, and the surface contact part is included in one of the pairs of aspects that have the largest magnitude area.

10. The viscoelasticity measuring apparatus according to claim 1, wherein the load detecting unit supports the driving unit and driving unit supports the indenter.

\* \* \* \* \*